United States Patent [19]

Takeuchi et al.

[11] Patent Number: 4,895,153

[45] Date of Patent: Jan. 23, 1990

[54] LOW FREQUENCY CURING APPARATUS APPLICABLE DIRECTLY TO ORGANISM

[75] Inventors: Mitsunori Takeuchi, Sagamihara; Minoru Sasaki, Yokohama, both of Japan

[73] Assignee: Kabushiki Kaisya Advance, Tokyo, Japan

[21] Appl. No.: 171,865

[22] Filed: Mar. 22, 1988

[30] Foreign Application Priority Data

Mar. 25, 1987 [JP] Japan .................................. 62-68956

[51] Int. Cl.$^4$ .......................... A61N 1/36; A61N 1/04
[52] U.S. Cl. ................................... 128/421; 128/422; 128/798
[58] Field of Search ................... 128/421, 422, 423 R, 128/420 R, 758, 802, 803

[56] References Cited

U.S. PATENT DOCUMENTS

| | | | |
|---|---|---|---|
| 3,077,884 | 2/1963 | Batrow et al. | 128/423 R |
| 4,210,150 | 7/1980 | James | 128/421 |
| 4,372,319 | 2/1983 | Ichinomiya et al. | 128/421 |
| 4,474,570 | 10/1984 | Ariura et al. | 128/798 X |

Primary Examiner—Lee S. Cohen
Attorney, Agent, or Firm—Finnegan, Henderson, Farabow, Garrett & Dunner

[57] ABSTRACT

A low frequency curing apparatus includes a power source; a boosted pulse generating unit for generating a train of boosted pulses in response to a first pulse signal; and accumulating unit for accumulating the boosted pulses to a predetermined amount; a low frequency pulse outputting unit for outputting the accumulated boosted pulses as low frequency pulses in response to a second pulse signal; a pair of electrode members able to be applied in a plane state to an object to be stimulated, for transmitting the low frequency pulses to the object; and a signal processing unit for outputting the first and second pulse signals based on a predetermined algorithm. A pulse width or a pulse interval of the first pulse signal or second pulse signal is changed, and as a result, a variety of low frequency stimulation effects can be applied to the object to be stimulated.

15 Claims, 20 Drawing Sheets

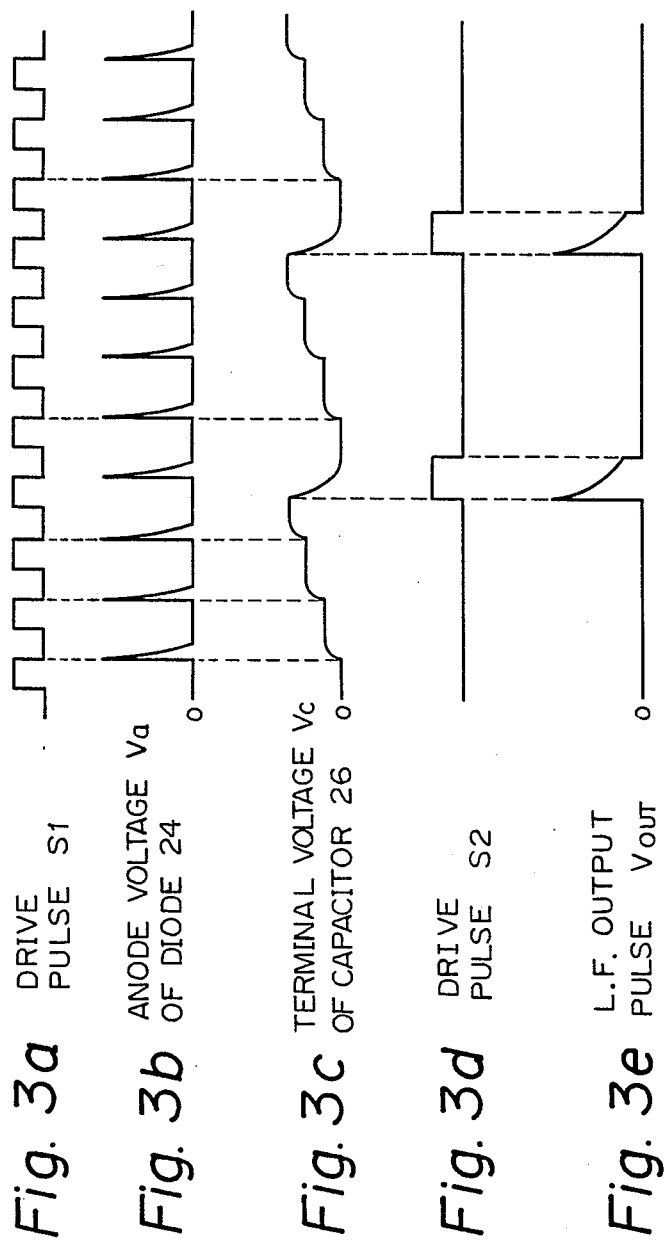

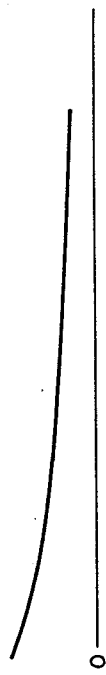
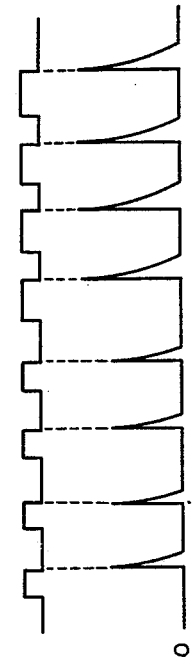
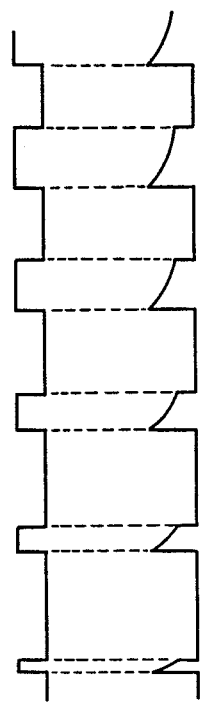
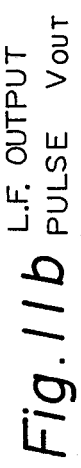
*Fig. 7a* VOLTAGE OF POWER SOURCE
*Fig. 7b* DRIVE PULSE C1
*Fig. 7c* BOOSTED PULSE
*Fig. 11a* DRIVE PULSE S2
*Fig. 11b* L.F. OUTPUT PULSE Vout

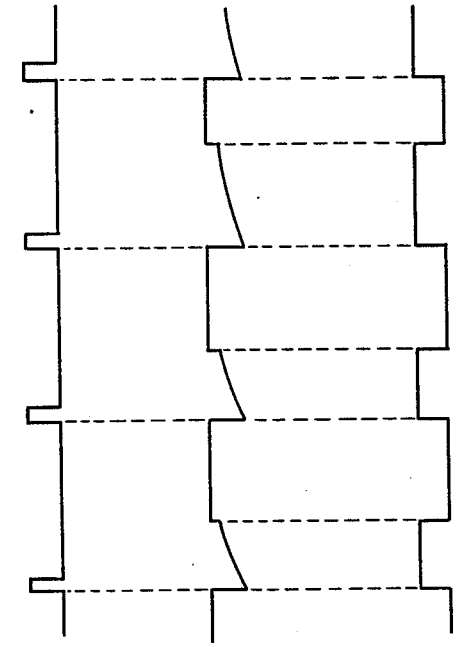
Fig. 9a BATTERY VOLTAGE K3
Fig. 9b OUTPUT OF SELECT CIRCUIT 56
Fig. 9c TERMINAL VOLTAGE OF CAPACITOR 84
Fig. 9d DRIVE PULSE S1

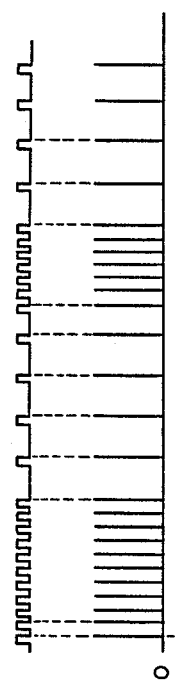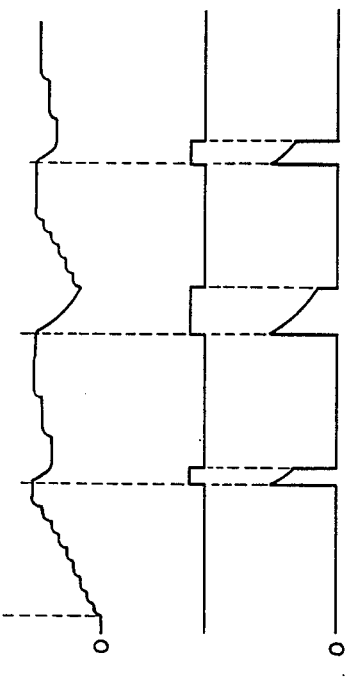
Fig.13a DRIVE PULSE S1
Fig.13b BOOSTED PULSE
Fig.13c VOLTAGE OF CAPACITOR 26
Fig.13d DRIVE PULSE S2
Fig.13e L.F. OUTPUT PULSE $V_{OUT}$

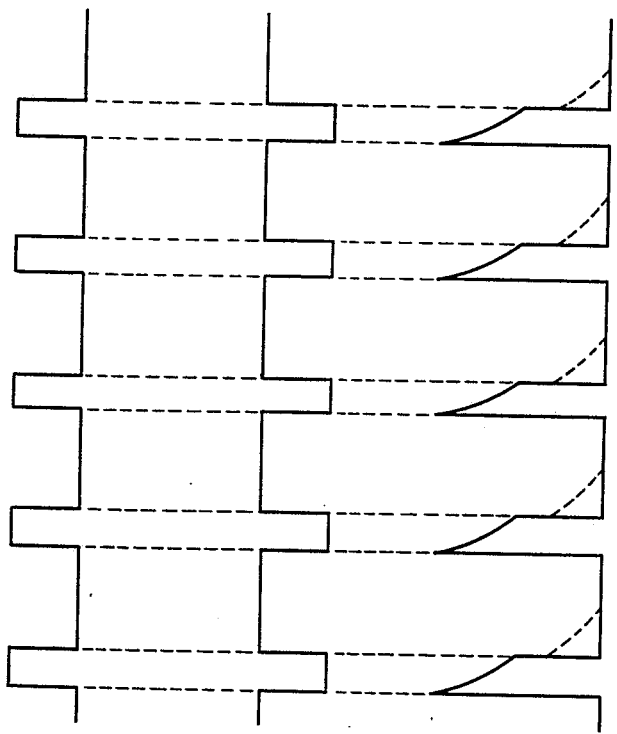
Fig. 14a DRIVE PULSE S2
Fig. 14b INVERTED SIGNAL S3 OF S2
Fig. 14c L.F. OUTPUT PULSE Vout

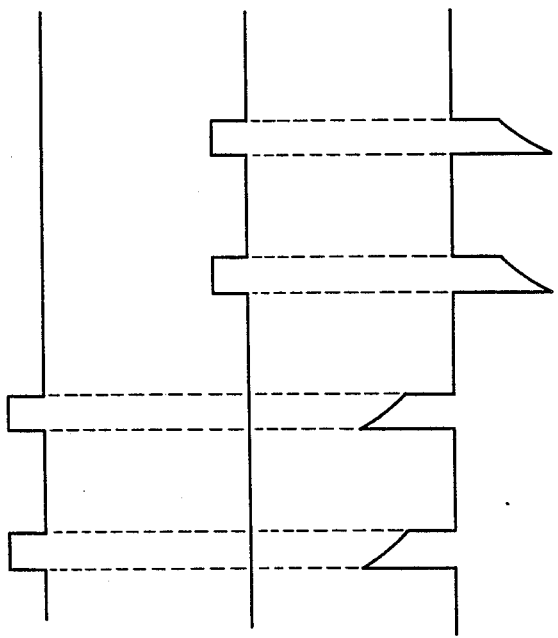

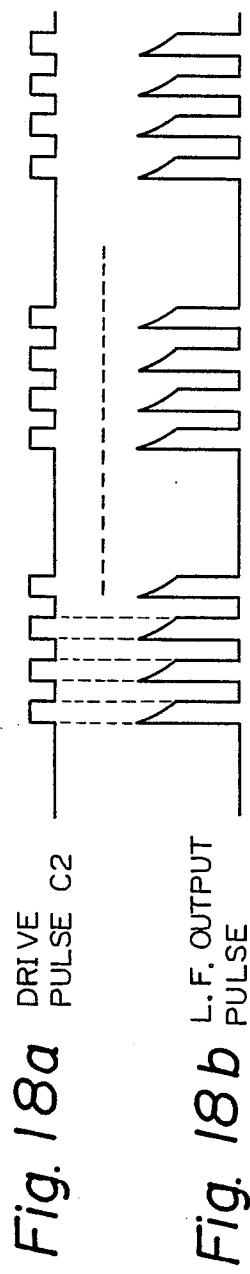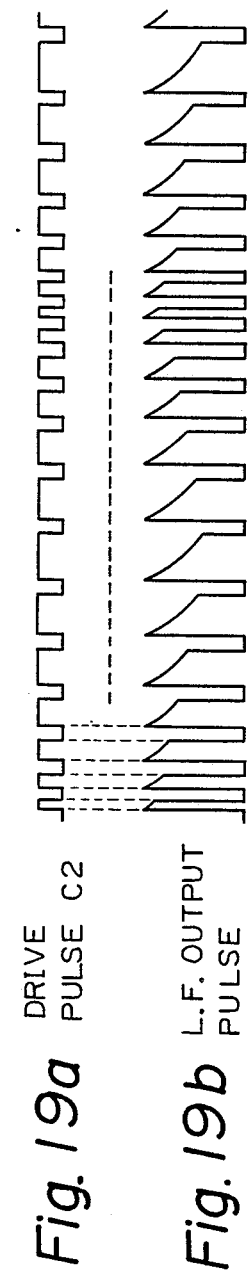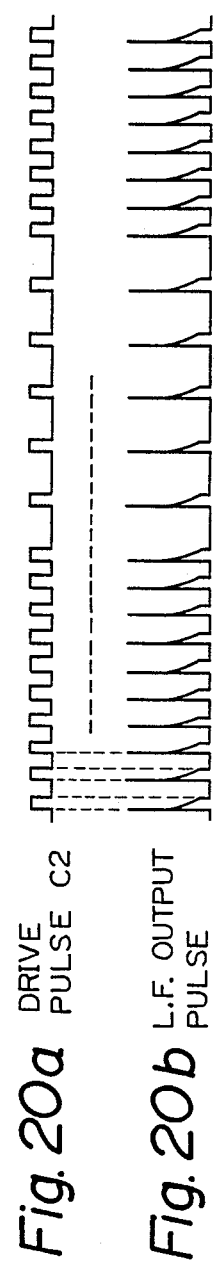
Fig. 18a DRIVE PULSE C2
Fig. 18b L.F. OUTPUT PULSE
Fig. 19a DRIVE PULSE C2
Fig. 19b L.F. OUTPUT PULSE
Fig. 20a DRIVE PULSE C2
Fig. 20b L.F. OUTPUT PULSE

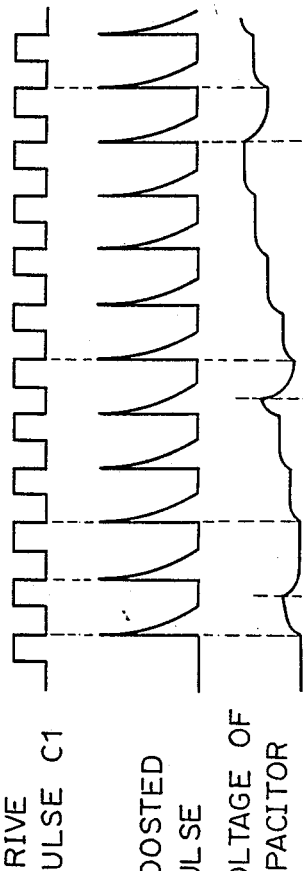
Fig.21a DRIVE PULSE C1
Fig.21b BOOSTED PULSE
Fig.21c VOLTAGE OF CAPACITOR
Fig.21d DRIVE PULSE C2
Fig.21e L.F. OUTPUT PULSE
Fig.21f DRIVE PULSE C1
Fig.21g DRIVE PULSE C2
Fig.21h L.F. OUTPUT PULSE

LOW FREQUENCY CURING APPARATUS APPLICABLE DIRECTLY TO ORGANISM

BACKGROUND OF THE INVENTION

1. Field of the Invention

The present invention relates to a small-sized low frequency curing apparatus capable of providing a required electrical stimulation to a subject such as an organism regardless of a small capacity of a power supply and, in particular, to a small-sized low frequency curing apparatus which can be applied directly to the organism and can be manufactured in the smallest possible size.

2. Description of the Related Art

Recently, use has been made of an endermic electrical stimulation apparatus, i.e., a so-called low frequency curing apparatus, which can apply acenesthesic stimulation to the skin at constant periods, and has a small size such that it can be applied to the skin in the form of a bandage, a poultice, and the like.

However, essentially such a low frequency curing apparatus should be constituted so that the electrical stimulation application mode can be changed to realize a stimulation effect similar to a finger-pressure treatment such as a massage. A constant or changeless stimulation causes a remarkable decrease in the degree of acenesthesia, thus lowering in the effectiveness of any cure. Accordingly, a small-sized low frequency curing apparatus capable of realizing a variety of stimulation effects is desired.

SUMMARY OF THE INVENTION

An object of the present invention is to provide an easily handled, small-sized low frequency curing apparatus capable of applying a variety of acenesthesic low frequency stimulation effects to an organism, and employing constituent elements and members which enable the high-density mounting necessary for any reduction in size of the apparatus.

The above-mentioned object is attained by providing a low frequency curing apparatus comprising: a small-sized power source; a boosted pulse generating unit connected to the small-sized power source, for generating a train of boosted pulses; an accumulating unit connected to the boosted pulse generating unit, for accumulating electrical energy to at least a predetermined amount at which a stimulation effect for an object to be electrically stimulated is attained; a low frequency pulse outputting unit connected to the accumulating unit, for outputting electrical energy accumulated in the accumulating unit as low frequency pulses; a pair of electrode members able to be applied in a plane state to the object to be stimulated, for transmitting the low frequency pulses from the low frequency pulse outputting unit to the object; and a signal processing unit connected to the small-sized power source, for carrying out a signal processing based on a predetermined algorithm and outputting a first pulse signal for driving the boosted pulse generating unit and a second pulse signal for driving the low frequency pulse outputting unit, a pulse width or a pulse interval of the first pulse signal or second pulse signal being changed, whereby a variety of low frequency stimulation effects are applied to the object to be stimulated.

BRIEF DESCRIPTION OF THE DRAWINGS

Other objects and features of the present invention will be described hereinafter in detail by way of preferred embodiments with reference to the accompanying drawings, in which;

FIGS. 3a to 3e are diagrams showing the signal waveform of each point in the apparatus shown in FIG. 2;

FIGS. 7a to 7c are diagrams showing the signal waveform for explaining an example of the operation of the signal processing means shown in FIG. 1;

FIGS. 9a to 9d are diagrams showing the signal waveform for explaining the operation of the circuit shown in FIG. 8;

FIGS. 11a and 11b are diagrams showing the signal waveform for explaining an example of the operation of the circuit shown in FIG. 10;

FIGS. 13a to 13e are diagrams showing the signal waveform for explaining an example of the operation of the circuits shown in FIGS. 12a to 12c;

FIGS. 14a to 14c are diagrams showing the signal waveform for explaining another example of the operation of the circuits shown in FIGS. 12a to 12c;

FIGS. 17a to 17c are diagrams showing the signal waveform for explaining an example of the operation of the circuit shown in FIG. 16;

FIGS. 18a and 18b, 19a and 19b, 20a and 20b, and 21a to 21h are diagrams showing the signal waveform for explaining a variety of output forms according to the apparatus of the present invention;

DESCRIPTION OF THE PREFERRED EMBODIMENTS

Figure 1:
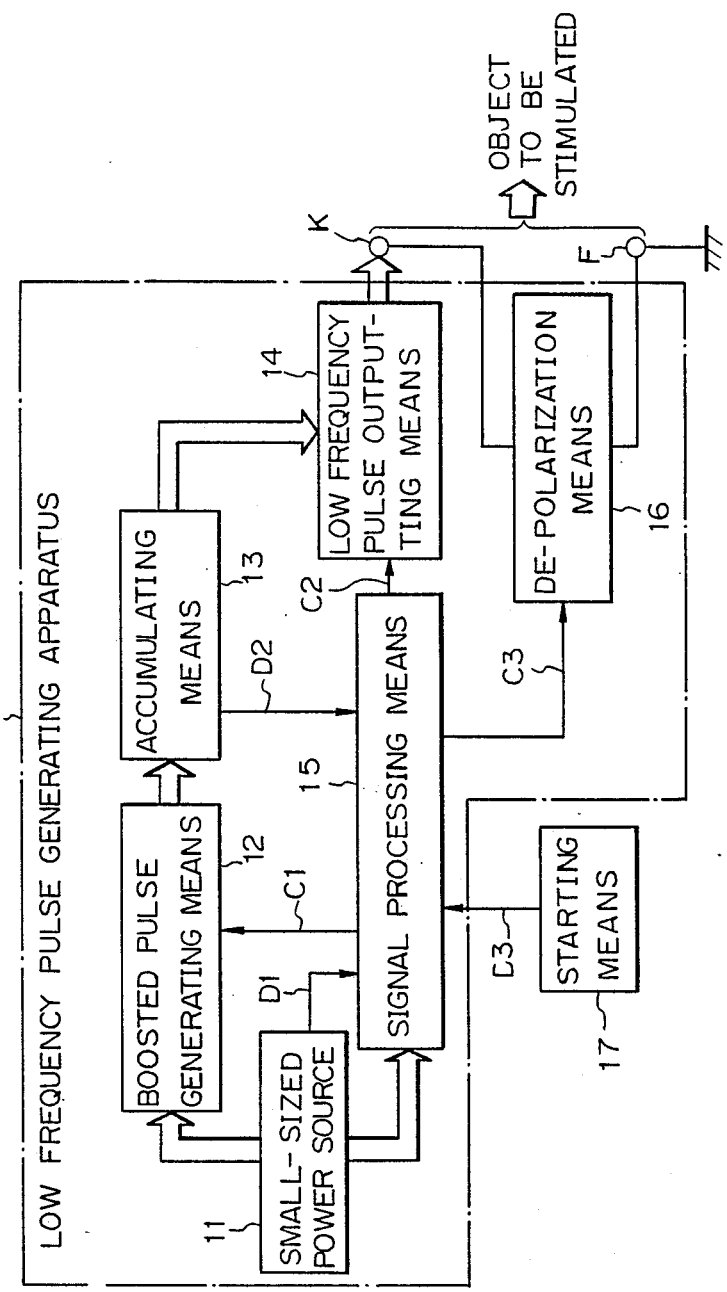
FIG. 1 is a block diagram schematically illustrating a constitution of the low frequency curing apparatus according to the present invention.

FIG. 1 schematically illustrates a constitution of the low frequency curing apparatus according to the present invention.

As a fundamental constitution, the apparatus of the present invention is constituted by a small-sized power source 11, a boosted pulse generating means 12, an accumulating means 13, a low frequency pulse outputting means 14, a signal processing means 15, and a pair of electrodes K and F. The electrode K participates in the curing, and the electrode F does not participate in the curing. Also, a de-polarization means 16 and a starting means 17 are preferably added to the above constitution in accordance with a variety of forms of implementation. Thick arrow marks shown in FIG. 1 indicate the flow of energy.

The small-sized power source 11 comprises a single or a plurality of button-type batteries, sheet-type batteries, coin-type batteries, cylinder-type batteries, pin-type batteries and the like. Although the configuration of the small-sized power source is not particularly restricted, a small-sized, thin-type and lightweight battery is preferable. Also, chargeable secondary batteries and the like can be used.

The boosted pulse generating means 12 comprises an oscillator generating a train of pulses and a boosting means consisting of, e.g., an inductor, which upon receipt of the power supply from the power source 11, generates a train of boosted pulses.

The accumulating means 13 comprises at least one capacitor for accumulating boosted pulses output from the boosted pulse generating means 12. Also, the means 13 can include a means for detecting energy accumulated in the capacitor, the constitution and operation of which will be described later.

The low frequency pulse outputting means 14 comprises a switching means such as a transistor and the like for transmitting the energy accumulated in the accumulating means 13 to the electrode K or stopping the flow of the energy.

Upon receipt of the power supply from the power source 11, the signal processing means 15 carries out a signal processing based on a predetermined algorithm and, based on the processing, controls the other means. As a fundamental control, the signal processing means 15 outputs a pulse signal C1 for driving the boosted pulse generating means and a pulse signal C2 for driving the low frequency pulse outputting means. Where a pulse width or a pulse interval of the pulse signal C1 or C2 is changed based on the above predetermined algorithm, the application mode of the low frequency output pulses applied via the electrode K to an object to be stimulated is varied. That is, a variety of low frequency stimulation effects can be realized by suitably selecting the pulse width and/or pulse interval of the signals C1 and/or C2

A chip is used as the signal processing means 15 employed in the present apparatus, the chip being approximately 5 or 6 mm² to 50 or 60 mm² and having a thickness of approximately 5 or 6 mm. For example, the signal processing means corresponds to; a microcomputer including a ROM for storing a program, a RAM, a CPU and the like; an ASIC realizing the above program or algorithm by a PLD, a gate array, standard cells and the like; a Look-Up Table (LUT) system in which pulse waveform data of the drive pulses is stored in advance in a memory element and the stored pulse waveform data is read out when needed; or a program sequencer generating the drive pulses based on a programmed algorithm; or the like. In one embodiment of the present invention, a general-purpose 4-bit CMOS microcomputer such as an SM-500, SM-590 or SM-591 produced by Sharp Corp., is preferably employed as the signal processing means.

The signal processing means is also capable of changing the algorithm included therein to another algorithm in response to input information given by another constituent element, as described later in detail.

For example, the signal processing means 15 receives input information D1 from the power source 11 and, based on an algorithm corresponding to the information D1, outputs the drive pulse C1 having a predetermined pulse width to the boosted pulse generating means 12. An example of the operation of the signal processing means is shown in FIGS. 7a to 7c in the form of signal waveforms. That is, when the voltage of the power source 11 gradually drops (see FIG. 7a), the signal processing means 15 outputs the drive pulse signal C1 having a gradually increased pulse width (see FIG. 7b). With the gradual increase of the pulse width of the signal C1, the boosted pulse generating means 12 outputs a boosted pulse signal so that the amplitude of the signal is gradually increased (see FIG. 7c). An explanation of the de-polarization means 16, starting means 17, a control signal C3, and input information D1, D2, and D3, will be given by way of various embodiments.

Figure 2:
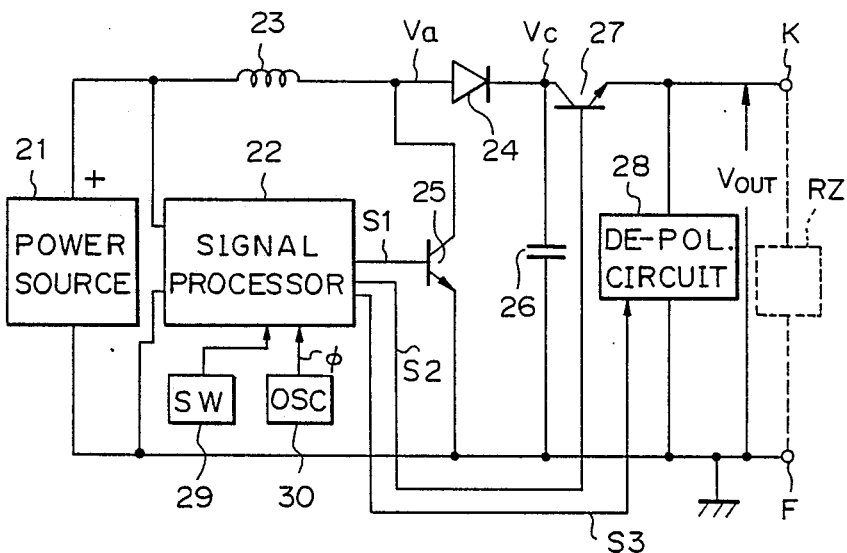
FIG. 2 is a circuit diagram illustrating a first embodiment of the present invention.

FIG. 2 illustrates a circuit constitution of a first embodiment of the present invention. In FIG. 2, a positive end of a power source 21 is connected to a signal processor 22 and one end of an inductor 23, and the negative end of the power source 21 is connected to the processor and grounded. The other end of the inductor 23 is connected to an anode of a diode 24 and a collector of an NPN transistor 25. An emitter of the transistor 25 is grounded and a base thereof responds to a drive pulse S1 (signal C1 in FIG. 1) output from the signal processor 22. A cathode of the diode 24 is connected to a collector of an NPN transistor 27 and one end of a capacitor 26, the other end of which is grounded. An emitter of the transistor 27 is connected to one end of a de-polarization circuit 28 an an electrode K participating in the curing process, and a base thereof responds to a drive pulse S2 (signal C2 in FIG. 1) output from the processor 22. The de-polarization circuit 28 responds to a drive pulse S3 (signal C3 in FIG. 1) output from the processor 22, and the other end thereof is connected to an electrode F not participating in the curing and grounded. Reference RZ equivalently indicates the impedance of the object to be stimulated, i.e, organism or body.

The power source 21 comprises one or a plurality of coin-type batteries, cylinder-type batteries, sheet-type batteries, pin-type batteries and the like. A battery or batteries employed in a portable apparatus such as an IC card, a memory card, a watch and the like is preferably used, as such a battery is the smallest possible battery available.

The signal processor 22, in accordance with a predetermined algorithm defined by a program and the like, can output the drive pulses S1 and S2 so that a pulse width or a pulse interval of the drive pulses can change with the lapse of time. Also, the processor 22 generates the drive signal S3 based on the drive signal S2 (see FIG. 5) and supplies the signal S3 to the de-polarization circuit 28. As a result, as will be described later in detail, polarization charges remaining within the organism are discharged through the de-polarization circuit. The signal processor 22 is provided with an input part 29 (starting means 17 in FIG. 1) and an oscillator (OSC) 30 for generating clock pulses. The input part 29 includes a number of switches (SW), e.g., a switch for starting or stopping the operation of the apparatus, a switch for selecting a pulse output mode, and the like.

The signal processor 22 can be constituted, for example, by a general-purpose one-chip microcomputer. In such a case, the processor 22 will comprise a ROM for storing a program to be executed, a RAM employed in executing the program, and a central processing unit (CPU) for generating the drive pulses S1 and S2 based on the program. The program represents an algorithm for setting a pulse mode of the drive pulses to be output and an algorithm for carrying out a combination of pulse modes. The pulse mode can be classified, for example, into the following functional routines; the increase or decrease of a pulse interval, the setting of a constant pulse interval, the increase or decrease of a pulse width, the setting of a constant pulse width, the change of an output end, and the like. When a select signal (signal D3 in FIG. 1) from the input part 29 is input to the CPU, the CPU sends an address signal to the ROM and calls the program therefrom, resulting in the generation of the drive pulses S1 and S2.

The de-polarization circuit 28 has the function of neutralizing polarization charges occurring within the organism when electrical stimulation is applied to the organism. For example, polarization charges can be neutralized by short-circuiting the electrodes K and F at a predetermined point during the time in which the pulses to be applied are OFF. The short-circuiting means may be a resistor, or a switching transistor which turns ON during the time in which the pulses to be applied are OFF.

Although, in the circuit illustrated in FIG. 2, the de-polarization circuit is connected across the electrodes K and F, the electrode K or F may be connected to the power source 21 to carry out a de-polarization, and thus the polarization charges are neutralized through the power source. In the case, since the power source is realized by a small capacity battery such as a sheet-type battery, a button-type battery and the like, the internal impedance thereof is very small. The output voltage of the power source is approximately 1.5 to 3 V, but the voltage appearing across the electrodes K and F as low frequency stimulation pulses is approximately 50 to 100 V. Accordingly, the voltage of the power source is approximately "0", compared with the output pulse voltage. That is, the power source is short-circuited.

In the constitution in which de-polarization is carried out through the power source, assuming that the power source is constituted by a secondary battery, charges flowing during the de-polarization operation can be collected and reutilized. The de-polarization circuit having a variety of forms is suitable selected in accordance with the use of the apparatus.

Next, the operation of the apparatus shown in FIG. 2 will be described with reference to FIGS. 3a to 3e.

The drive pulse S1 is output from the signal processor 22 in the form of a rectangular waver pulse, as shown in FIG. 3a. The transistor 25 turns ON or OFF in response to the drive pulse S1. When the transistor 25 turns ON and then turns OFF, a counter electromotive force (e.m.f.) of approximately 50 to 100 V is induced in the inductor 23, and as a result, boosted pulses as shown in FIG. 3appear at the anode of the diode 24. On the other hand, the drive pulse S2 is output from the signal processor 22 with a lower frequency than that of the drive pulse S1 as shown in FIG. 3d. The transistor 27 turns ON or OFF in response to the drive pulse S2. When the transistor 27 is OFF, the capacitor 26 accumulates boosted pulses via the diode 24, and thus the terminal voltage Vc thereof gradually rises as shown in FIG. 3c.

When the transistor 27 turns ON, the accumulated pulses or charges are applied via the electrode K to the load or organism RZ. The organism feels the applied low frequency (L.F.) pulses, shown in FIG. 3e, as an electrical stimulation effect. When the transistor 27 then turns OFF, charges remaining within the organism RZ are discharged and dissipated through the de-polarization circuit 28.

As mentioned above, the capacitor 26 accumulates the boosted pulses or charges during the time in which the drive pulse S2 applied to the transistor 27 is OFF, and it is possible to control the amount of accumulation or discharge of energy in accordance with a pulse width of the drive pulse S1 or S2. Therefore, it becomes possible to change a pulse width or a pulse interval of the L.F. output stimulation pulse by controlling a pulse width or interval of the drive pulse S1 or S2.

Assuming that the signal processor 22 for controlling the pulse width and interval of the drive pulse is constituted by the aforementioned general-purpose one-chip microcomputer, a program for the operation of the microcomputer becomes necessary.

An example of the program will be explained by way of flowcharts shown in FIGS. 4a and 4b.

Figure 4A:
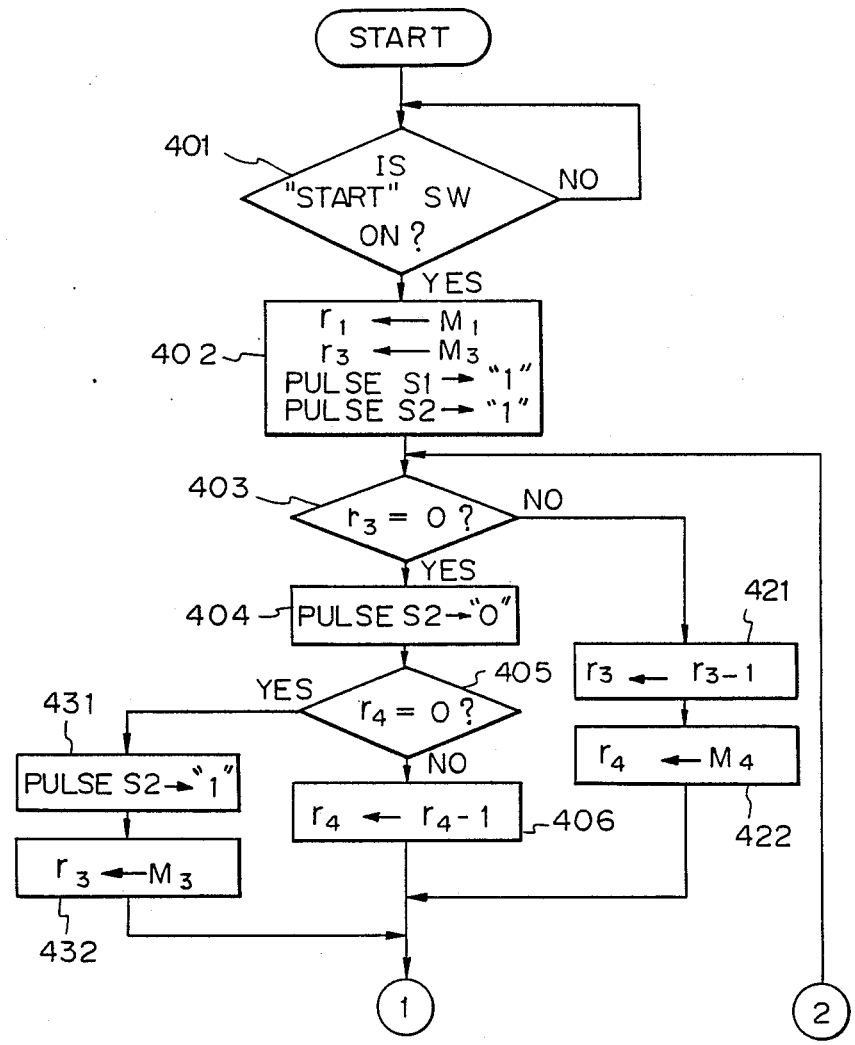
FIGS. 4a and 4b are flowcharts for explaining the operation of an example of the signal processor shown in FIG. 2.
Figure 4B:
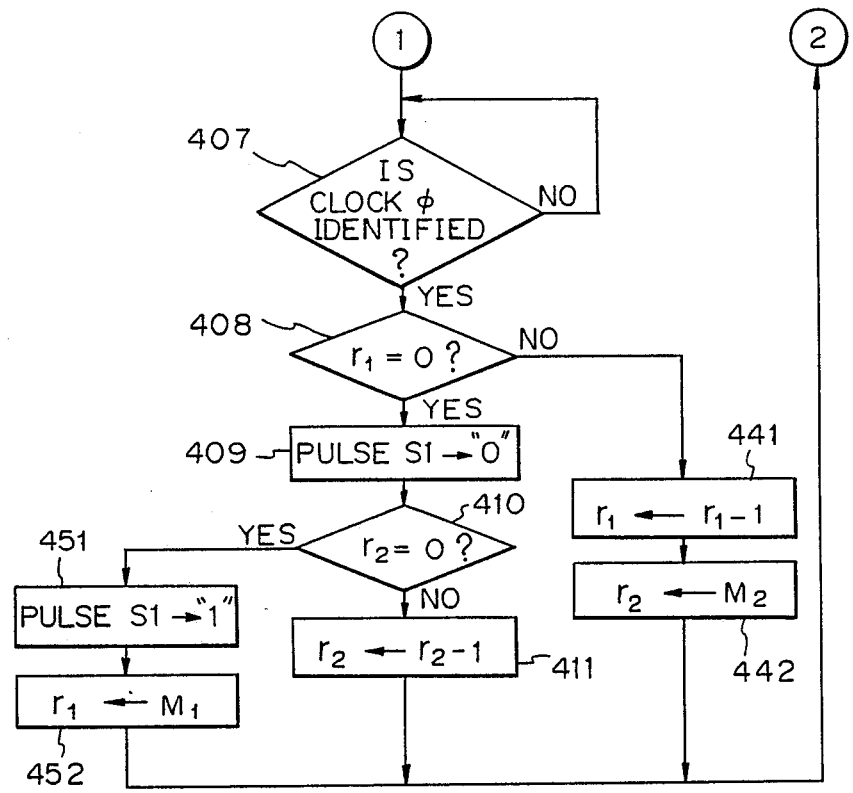

The flowcharts illustrated in FIGS. 4a and 4b represent a process for executing a control routine for the pulse width of the drive pulse and a control routine for the pulse interval thereof. Also, the signal processor 22 can execute a routine for an inversion of the polarity of the L.F. output pulse or a routine for an increase or decrease of the pulse interval, although the process for executing each routine is not shown in the attached drawings. Parameters for the control of the pulse width and interval are stored in advance in the ROM. In the present example, each parameter is set as follows: $M_1$ defines the pulse width of the drive pulse S1; $M_2$ defines the pulse interval of the pulse S1; $M_3$ defines the pulse width of the drive pulse S2; and $M_4$ defines the pulse interval of the pulse S2. Also, memories or registers (not shown) included in the microcomputer are indicated by references $r_1$, $r_2$, $r_3$, and $r_4$.

Referring to FIGS. 4a and 4b, at step 401, the signal processor 22 or microcomputer determines whether or not a "start" SW is ON at the input part 19. If the result is YES, the control advances to step 402, and if the result is NO, the control returns to step 401. At step 402, the data of $M_1$ is set to the memory $r_1$ and the data of $M_3$ is set to the memory $r_3$. Also, as drive pulses S1 and S2, respectively, signals having a logical "1" or high level are output. At step 403, the micro-computer determines whether or not the value stored in the memory $r_3$ is zero (0). If the result is YES, the control advances to step 404, and if the result is NO, the control advances to step 421. At step 404, a signal of having a logical "0" or low level is output as the drive pulse S2. Then, at step 405, the microcomputer determines whether or not the value stored in the memory $r_4$ is zero (0). If the result is YES, the control advances to step 431, and if the result is NO, the control advances to step 406. At step 406, "1" is subtracted from the value of the memory $r_4$ and the resulting value is stored in the memory $r_4$. Then, the control advances to step 407.

On the other hand, at step 421, "1" is subtracted from the value of the memory $r_3$ and the resulting value is stored in the memory $r_3$, and at the next step 422, the data of $M_4$ is set to the memory $r_4$ and the control then advances to step 407.

At step 431, a logical "1" or high level signal is output as the drive pulse S2. At the next step 432, the data of $M_3$ is set to the memory $r_3$ and the control then advances to step 407.

At step 407, the microcomputer determines whether or not the clock pulses $\phi$ have been generated by the oscillator 30. If the clock $\phi$ has been generated, the control advances to step 408, and if the clock $\phi$ has not been generated, the control returns to step 407. At step 408, the microcomputer determines whether or not the value stored in the memory $r_1$ is zero (0). If the result is YES, the control advances to step 409, and if the result is NO, the control advances to step 441. At step 409, a logical "0" or low level signal is output as the drive pulse S1. Then, at step 410, the microcomputer determines whether or not the value stored in the memory $r_2$ is zero (0). If the result is YES, the control advances to step 451, and if the result is NO, the control advances to step 411. At step 411, "1" is subtracted from the value of the memory $r_2$ and the resulting value is stored in the memory $r_2$. Then, the control returns to step 403.

On the other hand, at step 441, "1" is subtracted from the value of the memory $r_1$ and the resulting value is stored in the memory $r_1$. At the next step 442, the data of $M_2$ is set to the memory $r_2$ and the control then returns to step 403.

At step 451, a logical "1" or high level signal is output as the drive pulse S1. At the next step 452, the data of $M_1$ is set to the memory $r_1$ and the control then returns to step 403.

As explained above, it is possible to generate drive pulses S1 and S2 having a desired pulse width and a desired pulse interval by suitably selecting the values of the parameters $M_1$, $M_2$, $M_3$, and $M_4$.

Although, in the above example, the signal processor 22 is constituted by a general-purpose one-chip microcomputer, it also may be constituted by a hardware circuit constitution.

Figure 5:
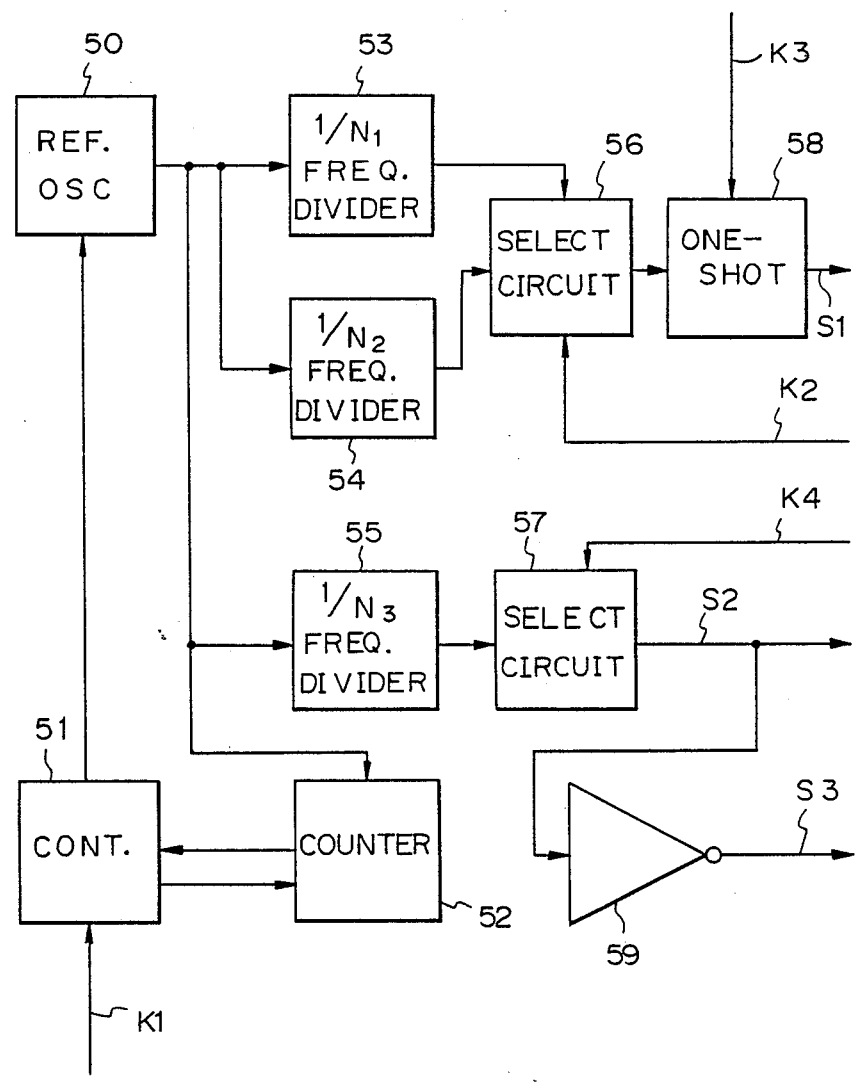
FIG. 5 is a block diagram illustrating a constitution of another example of the signal processor shown in FIG. 2.

FIG. 5 illustrates a block diagram of a constitution of an example of the signal processor shown in FIG. 2, which can be preferably minimized for an IC such as a gate array.

In FIG. 5, reference 50 denotes a reference oscillator, which corresponds to the oscillator 30 in FIG. 2 and oscillates pulses $\phi$. The oscillated pulses $\phi$ are input to a $1/N_1$ frequency divider 53, a $1/N_2$ frequency divider 54, a $1/N_3$ frequency divider 55, and a counter 52. Reference 56 denotes a select circuit, which selects one of the outputs of the $1/N_1$ frequency divider 53 and $1/N_2$ frequency divider 54 in response to an external input signal K2 (signal D3 in FIG. 1). The selected output is input to a mono-stable multivibrator or one-shot 58 and used as a trigger signal for the one-shot. The one-shot 58, in response to the output signal of the select circuit 56, generates a drive pulse signal S1 having a certain width based on an external input signal K3 (signal D3 in FIG. 1) for defining the pulse width.

On the other hand, reference 51 denotes a controller, which controls the oscillator 50 and the counter 52 in response to an external input signal K1 (signal D3 in FIG. 1). As one function thereof, the controller 51 supplies the oscillator 50 with a control signal for starting the oscillation thereof in response to a first external input signal K1. As another function thereof, the controller 51 supplies the counter 52 with a control signal for starting the counting operation thereof in response to a second external input signal K1. Upon receipt of the control signal, the counter 52 counts the pulses oscillated from the reference oscillator 50, and the value counted during the counting operation is monitored by the controller 51. When the counted value reaches a predetermined value, the controller 51 supplies the oscillator 50 with a control signal for stopping the oscillation thereof.

Reference 57 denotes a select circuit, which receives the output of the $1/N_3$ frequency divider 55, selects one of a plurality of values internally defined (not shown in FIG. 5) in response to an external input signal K4 (signal D3 in FIG. 1) for defining a pulse width, and generates a drive pulse signal S2 having that pulse width. A concrete circuit constitution of the select circuit 57 will be described later. Reference 59 denotes an inverter, which inverts the logic level of the drive signal S2 and outputs a control signal S3. The control signal S3 is input to the de-polarization circuit 28 shown in FIG. 2.

The frequency of the reference oscillator 50 is set to approximately 20 kHz, where that of the drive pulse S1 is set to 10 kHz and that of the drive pulse S2 is set to approximately 10 Hz. As a result, a satisfactory cure by the L.F. curing apparatus can be realized. Also, the drive pulses S1 and S2 are generated based on the frequency division of the reference pulse signal $\phi$. Accordingly, it is possible to generated the drive pulses S1 and S2 having a desired pulse width and a desired pulse interval by suitably charging the ratio of each of the frequency dividers 53, 54, and 55.

Furthermore, although, the signal processor illustrated in FIG. 5 is constituted to generate the drive pulses S1 and S2 independently of each other, it may be constituted to generate these pulse in dependence on each other. For example, there a means may be added which counts the drive pulses S1 by another counter, and causes the drive pulses S2 to be output when the counted value reaches a predetermined value. By adding such means, and suitably selecting one of the additionally provided means and the originally provided drive pulse generating means in response to the command from the input part 29 shown in FIG. 2, a variety of pulse output modes can be realized.

Additionally, the external input signals K1, K2, K3 and K4 shown in FIG. 5 correspond to the input signals output from the input part 29 shown in FIG. 2. However, the external input signals shown in FIG. 5 are not only artificial input signals, but also input signals containing functional information as described later.

Next, the operation of the signal processor shown in FIG. 5 will be described.

The frequency of the pulse signal output from the reference oscillator 50 is divided into $1/N_1$, $1/N_2$, and $1/N_3$, respectively, in the frequency dividers 53, 54, and 55. The $1/N_1$ signal and $1/N_2$ signal are input to the select circuit 56, where one of the signals is selected in response to the external input signal K2. The selected signal is input to the one-shot 58 as a trigger. Upon receipt of the trigger, the one-shot 58 outputs the drive pulse S1 based on the external input signal K3. On the other hand, the $1/N_3$ signal output from the frequency divider 55 is input to the select circuit 57, where the pulse signal having a pulse width based on the external input signal K4 is generated and output as the drive pulse S2.

The counter 52 starts counting in response to the control signal from the controller 51, and the controller 51 monitors the counted value during the counting operation and sends a "stop" control signal to the oscillator 50 when the counted value reaches a predetermined value, and as a result, the oscillation of the pulses is stopped. That is, the drive pulses S1 and S2 are generated until the predetermined value is reached. Therefore, by suitably selecting the predetermined value, it is possible to realize an optimum curing time according to the state of the organism.

Figure 6:
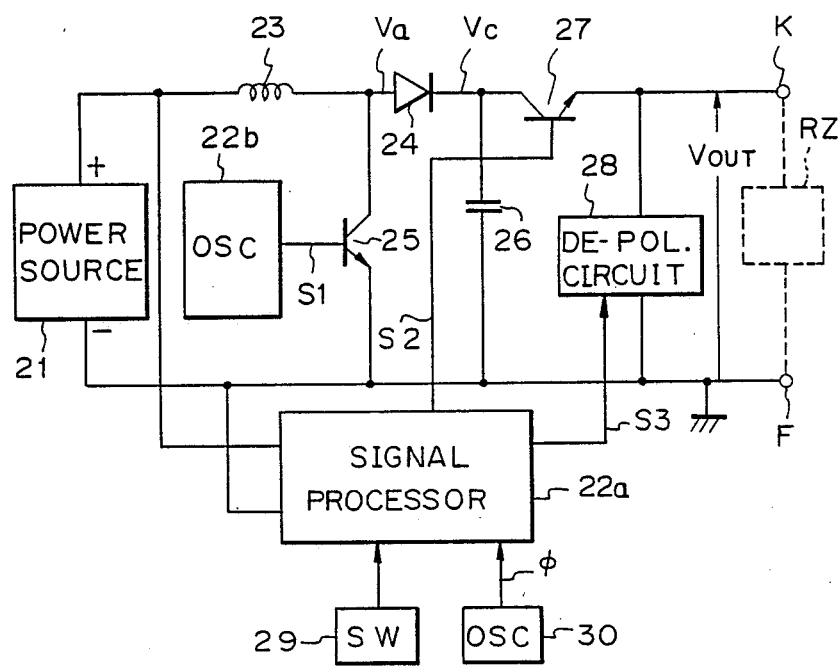
FIG. 6 is a circuit diagram illustrating a modification of the apparatus shown in FIG. 2.

FIG. 6 illustrates a circuit constitution of a modification of the apparatus shown in FIG. 2.

The difference between the present apparatus and the apparatus shown in FIG. 2 is that, in place of the signal processor 22, a signal processor 22a and an oscillator 22b including a multivibrator and the like are provided. Namely, although in the apparatus of FIG. 2 the transistor 25 is driven by the signal S1 from the signal processor 22, in the present example, it is driven by a drive signal S1 from the oscillator 22b. Other constituent elements and the feature of the operation are the same as those in FIG. 2 and, accordingly, an explanation thereof is omitted.

Figure 8:
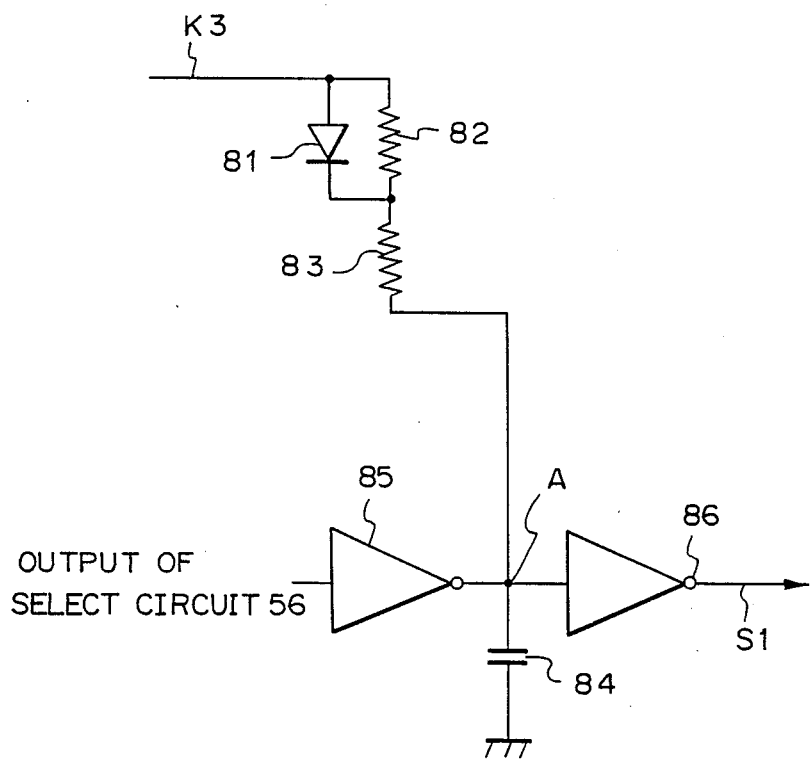
FIG. 8 is a circuit diagram illustrating an example of the constitution of the one-shot shown in FIG. 5.

FIG. 8 illustrates an example of the circuit constitution of the one-shot 58 shown in FIG. 5 and shows in detail a circuit which can increase the pulse width of the drive pulse S1 when the voltage of the power source, i.e., the battery, drops to a certain level.

In FIG. 8, reference K3 denotes an external input signal representing the battery voltage (signal D1 in FIG. 1) which is input to an anode of a diode 81 and one end of a resistor 82. A cathode of the diode 81 is connected to the other end of the resistor 82, and connected via a resistor 83 to one end of a capacitor 84, indicated by reference A. The other end of the capacitor 84 is grounded. On the other hand, the signal output from the select circuit 56 is input to an inverter 85, the output of which is input via the point A to an inverter 86. The output of the inverter 86 is used as the drive pulse S1.

Next, the operation of the circuit shown in FIG. 8 will be described with reference to FIGS. 9a to 9d.

When the signal output from the select circuit 56 is low level, i.e., a trigger signal is not input, the output end of the inverter 85 is high level, and the drive pulse S1 is low level. When the high level signal, i.e., the trigger signal, is input to the inverter 85, the output end of the inverter 85 falls to low level, and the drive pulse S1 rises to a high level. When the trigger signal then falls to the low level, the output end of the inverter 85 rises to the high level. At this time, the capacitor 84 is charged via the diode 81 and/or resistor 82, and the resistor 83 by the external input signal K3 representing the battery voltage. The potential at the point A, i.e. the terminal voltage of the capacitor 84, is gradually raised by the charging into the capacitor 84. When the potential reaches a threshold voltage, the output signal of the inverter 86, i.e. the drive pulse S1, falls to a low level.

Assuming that the battery voltage gradually falls due to deterioration, leakage of charges, and the like, as shown in FIG. 9a.

Initially, when the battery voltage is relatively high, the voltage across the resistor 82 becomes higher than the forward-direction voltage of the diode 81 due to the charging into the capacitor 84, and as a result, the charging current flows via the diode 81, the resistor 82, and the resistor 83 into the capacitor 84.

Conversely, when the battery voltage drops and the voltage across the resistor 82 becomes lower than the forward-direction voltage of the diode 81, the current flowing through the diode ceases, resulting in a decrease in the charging current. That is, when the battery voltage drops to a predetermined level, the whole charging current into the capacitor 84 is reduced, and thus the time required for charging the capacitor is increased. This causes the pulse width of the drive pulse S1 to be increased, as shown in FIGS. 9c and 9d.

Figure 10:
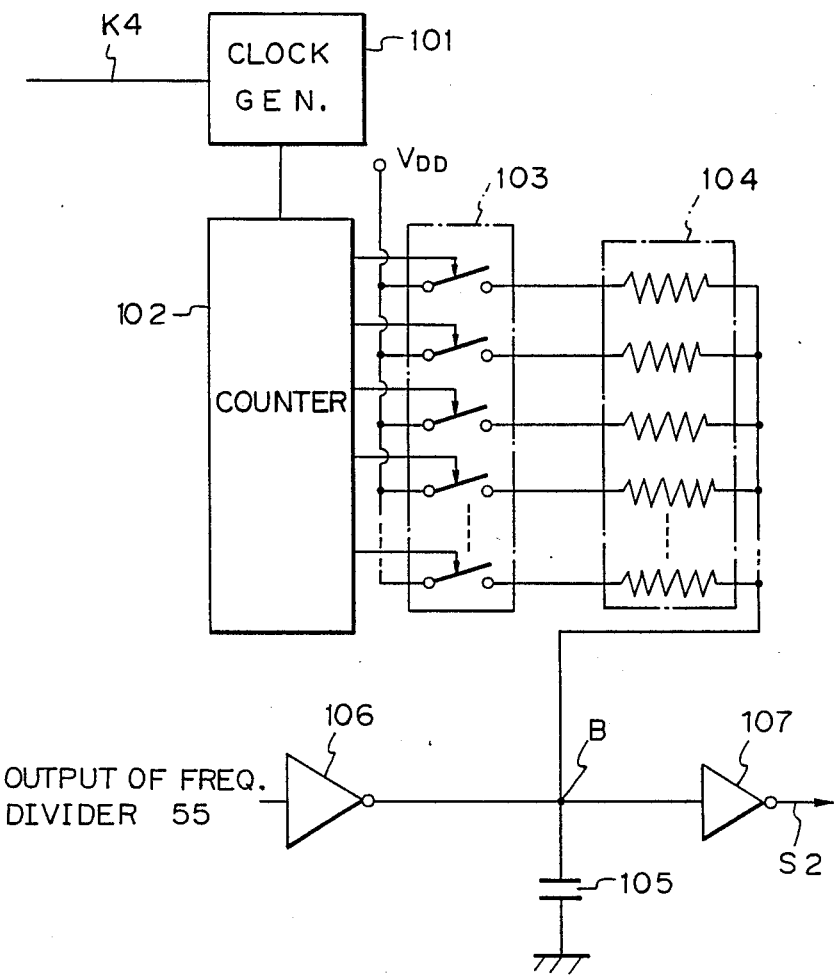
FIG. 10 is a circuit diagram illustrating an example of the constitution of the select circuit 57 shown in FIG. 5.

FIG. 10 illustrates an example of the constitution of the select circuit 57 shown in FIG. 5.

In FIG. 10, reference K4 denotes an external input signal representing the signal for starting the operation of the circuit, or the signal for changing the pulse output mode. The signal K4 is input to a clock generator 101, which outputs clock pulses at predetermined time intervals. Reference 102 denotes a counter, which counts pulses output from the generator 101, and outputs a sequence of select signals in accordance with the counted value. Reference 104 denotes a resistance means consisting of a plurality of resistors, one end of each being commonly connected. Reference 103 denotes a switch means consisting of switches, the number of which corresponds to the number of the resistors. The switch means 103 sequentially closes each of the switches in response to the select signals from the counter 102, and supplies the corresponding resister with the battery voltage $V_{DD}$. The commonly connected point of the resistors, i.e., point B, is connected to one end of capacitor 105. The other end of the capacitor 105 is grounded. On the other hand, the 1/N3 signal output from the frequency divider 55 is input to an inverter 106, the output of which is input via the point B to an inverter 107. The output of the inverter 107 is used as the drive pulse S2.

Next, the operation of the circuit shown in FIG. 10 will be described.

Upon receipt of the clock pulses output from the generator 101 in response to the signal K4, the counter 102 starts counting and outputs a voltage having a level corresponding to the counted value, as the select signal. The switch means 103 closes a specific switch in response to the select signal, and as a result, the battery voltage $V_{DD}$ is applied via the specific switch to the corresponding resistor. That is, the current based on the battery voltage $V_{DD}$ flows via the selected switch and the corresponding resistor into the capacitor 105. Therefore, the charging time of the capacitor 105 is changed depending upon the switch selection. Namely, the drive pulse S2 can have a pulse width corresponding to the time constant determined by a combined resistance in the resistance means 104 and a capacitance of the capacitor 105.

When the 1/N3 signal output from the frequency divider 55 is at a low level, the output end of the inverter 106 is at a high level, and the drive pulse S2 at a low level. When the high level signal, i.e., the trigger signal, is input to the inverter 106, the output end of the inverter 106 falls to a low level, and the drive pulse S2 rises to a high level. When the trigger signal then falls to a low level, the output end of the inverter 106 rises to a high level. At this time, the capacitor 105 is charged by the battery voltage $V_{DD}$ via the combined resistance selected in the resistance means 104. The potential at the point B is gradually raised by the charging into the capacitor 105, and when the potential reaches a threshold voltage, the output signal of the inverter 107, i.e. the drive pulse S2, falls to a low level.

As explained above, it is possible to change the charging time of the capacitor 105 by suitably selecting the switches and changing the value of the combined resistance, and thus to give the drive pulse S2 a desired pulse width. For example, as shown in FIGS. 11a and 11b, it is possible to gradually increase the pulse width of the drive pulse S2, and although not shown in the attached drawings, it is possible to gradually decrease the pulse width thereof. By employing such a control, the degree of cenesthesia can be changed with the lapse of time.

Figure 12A:
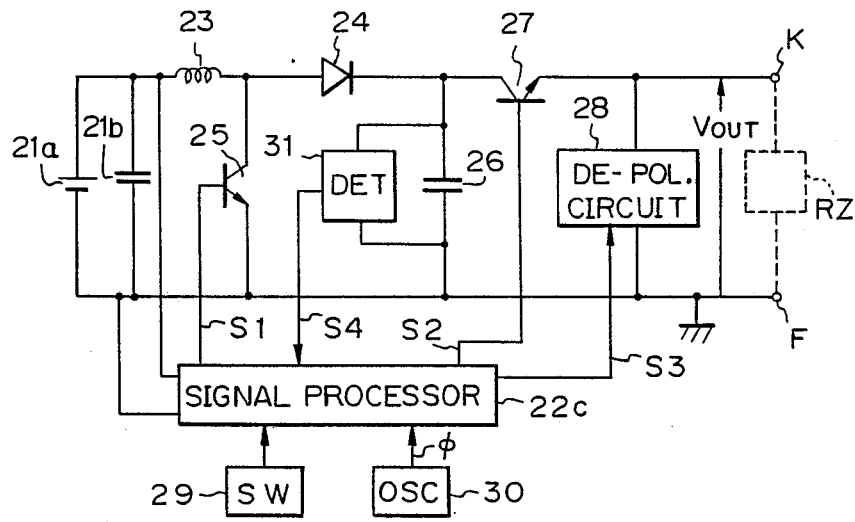
FIGS. 12a to 12c are circuit diagrams illustrating a second embodiment of the present invention.
Figure 12B:
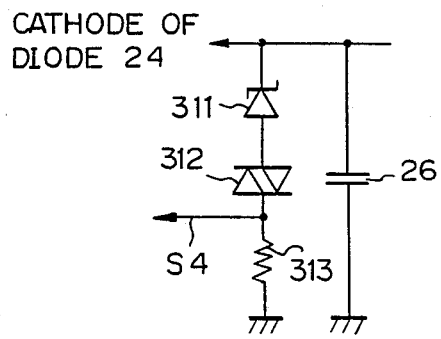
Figure 12C:
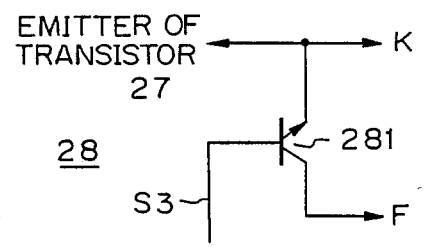

FIG. 12a illustrates a circuit constitution of a second embodiment of the present invention. In detail, FIG. 12a shows a circuit which can change the form of the generation of the drive pulse S1 in accordance with energy accumulated in the accumulating means (capacitor 26); FIG. 12b shows an example of the circuit constitution of a means (DET) for detecting the accumulated electrical energy, indicated by reference 31 in FIG. 12a; and, FIG. 12c shows an example of the de-polarization circuit 28 shown in FIG. 12a.

Referring to FIGS. 12a and 12b, the cathode of the diode 24 is connected to a cathode of a Zener diode 311, an anode of which is connected to one end of a trigger diode 312 such as a DIAC, SSS and the like. The other end of the trigger diode 312 is grounded via a resistor 313. The connection point between the trigger diode 312 and the resistor 313 is used as an output end for outputting a control signal S4. The control signal S4 corresponds to the signal D2 in FIG. 1, or the signal K2 in FIG. 5. Note, the Zener diode 311 may be omitted.

The capacitor 26 is charged by boosted pulses input through the diode 24. In the charging process, when the terminal voltage of the capacitor 26 exceeds the sum of the Zener voltage of the diode 311 and the breakdown voltage of the trigger diode 312, the trigger diode 312 is made ON, and as result, the logic level of the control signal S4 is changed from low level to high level. The signal processor 22c, in response to the high level control signal S4, causes the select circuit 56 (see FIG. 5) to select either of the frequency divider 53 or 54, and to change the period of the trigger signal to be applied to the one-shot 58, and as a result, the drive pulse S1 according to the period of the trigger signal is applied to the transistor 25, and the capacitor 26 is charged or discharged according to the period of the ON-OFF operation of the transistor 25.

Therefore, where the ratio of the frequency divider selected by the select circuit 56 is set such that the pulse interval of the drive pulse S1 is relatively long, it is possible to effectively utilize the drive pulse S1, as shown in FIGS. 13a to 13e. This is because, if the pulse interval of the signal S1 is relatively short, the capacitor 26 cannot effectively accumulate charges due to the saturation characteristics thereof.

Also, in the circuit constitution illustrated in FIG. 12a, when the curing time is predetermined, the command signal from the input part 29, corresponding to the signal D3 from the starting means 17 shown in FIG. 1, is input to the signal processor 22c. Thus, when the predetermined time has elapsed, the oscillation of the drive pulse S2 is stopped and the curing is finished.

Next, referring to FIGS. 12a and 12c, the de-polarization circuit 28 comprises an NPN transistor 281. An emitter of the transistor 281 is connected to the emitter of the transistor 27 and the electrode K, and a collector thereof is connected to the electrode F. The transistor 281 responds to the control signal S3 from the signal processor 22c, and discharges the polarization charges remaining the load, i.e., the organism RZ, after the L.F. stimulation pulses are applied to the organism.

When the drive pulse S2 changes from low level to high level, the transistor 27 turns ON and the charge accumulated in the capacitor 26 is applied via the transistor 27 to the load RZ, i.e., the organism. At this time, polarization charges occur in the organism. When the drive pulse S2 then falls to a low level, i.e., the control signal S3 rises to a high level (see FIG. 5), the transistor 27 turns OFF and the transistor 281 turn ON, and as a result, charges remaining within the organism are discharged via the electrode K, transistor 281, and electrode F. Namely, the de-polarization circuit 28 operation starts in response to the fall of the drive pulse S2, as shown in FIGS. 14a to 14c, and the polarization charges are neutralized. Further, the portion indicated by the broken line in FIG. 14c shows a waveform when the de-polarization operation is not carried out.

As explained above, by suitably setting an internal algorithm in the signal processor 22c (signal processing means 15 in FIG. 1), it becomes possible to generate a signal S3 (signal C3 in FIG. 1) other than the drive pulses S1 and S2 (signals C1 and C2 in FIG. 1).

Figure 15:
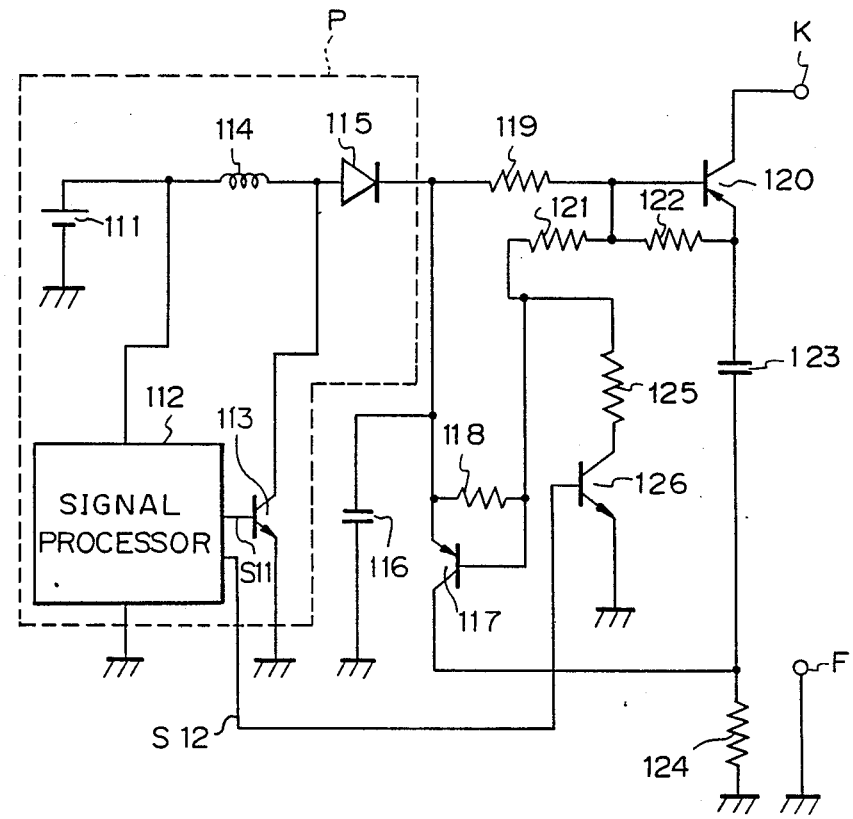
FIG. 15 is a circuit diagram illustrating a third embodiment of the present invention.

FIG. 15 illustrates a circuit constitution of a third embodiment of the present invention. In detail, FIG. 15 shows a circuit which can be increase the energy of the L.F. output pulse.

In FIG. 15, the portion P indicated by a broken line represents a boosted pulse generating circuit, which is constituted by a small-sized battery 111, a signal processor 112, an NPN transistor 113, an inductor 114, and a diode 115. The negative end of the battery 111 is grounded and the positive end thereof is connected to the signal processor 112 and one end of the inductor 114. The other end of the inductor 114 is connected to an anode of the diode 115 and a collector of the transistor 113. An emitter of the transistor 113 is grounded and a base thereof responds to a drive pulse S11 (signal C1 in FIG. 1) output from the processor 112.

A cathode of the diode 115 is connected to one end of a capacitor 116, an emitter of a PNP transistor 117, one end of a resistor 118, and one end of a resistor 119. The other end of the capacitor 116 is grounded, and a collector of the transistor 117 is grounded via a resistor 124. On the other hand, the other end of the resistor 119 is connected via a resistor 121 to a base of the transistor 117 and the other end of the resistor 118, and connected to a base of a PNP transistor 120 and one end of a resistor 122. A collector of the transistor 120 is connected to the electrode K, and an emitter thereof is connected to the other end of the resistor 122 and one end of a capacitor 123. The other end of the capacitor 123 is grounded via the resistor 124. Also, the base of the transistor 117 is connected via a resistor 125 to a collector of an NPN transistor 126. An emitter of the transistor 126 is grounded and a base thereof responds to a drive pulse S12 (signal C2 in FIG. 1) output from the processor 112. Another electrode F is grounded.

Next, the operation of the apparatus shown in FIG. 15 will be described.

When the drive pulse S12 is not output, the transistor 126 is made OFF and the transistors 117 and 120 are also made OFF. On the other hand, the transistor 113 turns ON and OFF in response to the drive pulse S11, resulting in the appearance of boosted pulses at the cathode of the diode 115. The boosted pulses are accumulated in the capacitor 116 and, via the resistance 119 and 122, in the capacitor 123.

When the drive pulse S12 is output from the signal processor 112 and supplied to the base of the transistor 126, the transistor 126 turns ON and lowers the collector level thereof. Namely, the base level of the transistor 117 is lowered, so that the transistor 117 turns ON.

Accordingly, one end of the capacitor 116 is connected via the transistor 117 in series to the capacitor 123. Also, since the collector level of the transistor 126 is lowered, the base level of the transistor 120 is lowered via the resistors 125 and 121, so that the transistor 120 is made ON state. Therefore, electrical energy accumulated in the capacitors 116 and 123 connected in series is applied via the transistor 120 to the electrode K. Assuming that each capacitance of the capacitors 116 and 123 is the same, the voltage of the L.F. stimulation pulse becomes twice the voltage of the accumulated boosted pulse.

Figure 16:
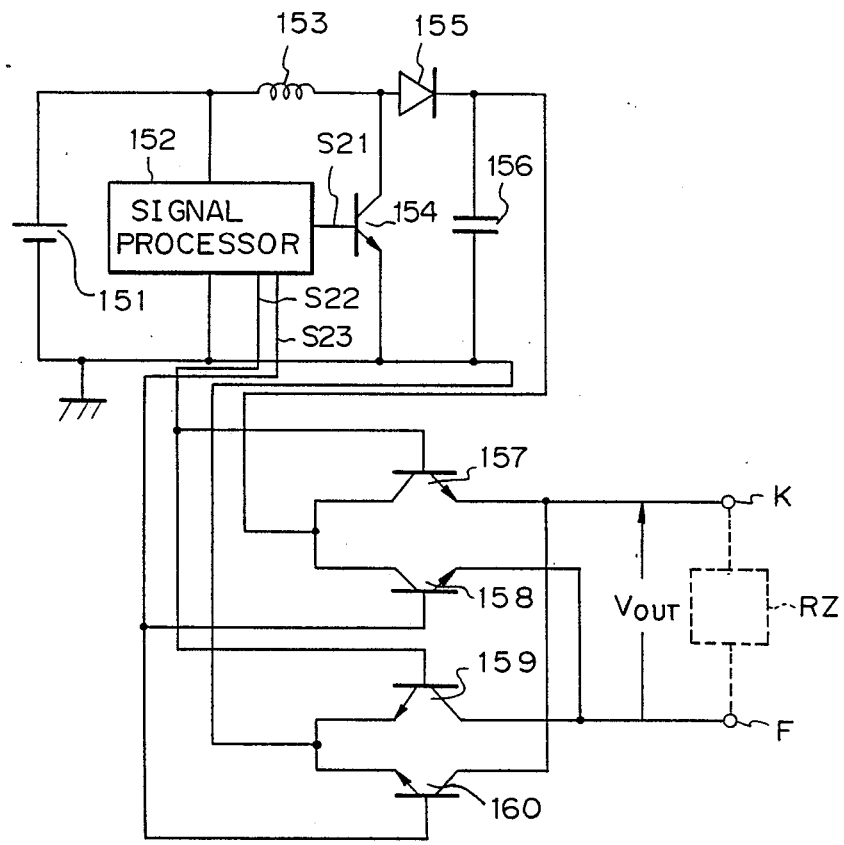
FIG. 16 is a circuit diagram illustrating a fourth embodiment of the present invention.

FIG. 16 illustrates a circuit constitution of a fourth embodiment of the present invention. In detail, FIG. 16 shows a circuit which can invert the polarity of the L.F. output pulse using drive pulses generated by a signal processor.

In FIG. 16, the positive end of a battery 151 is connected to a signal processor 152 and one end of an inductor 153. The other end of the inductor 153 is connected to a collector of an NPN transistor 154 and an anode of a diode 155. A cathode of the diode 155 is connected to one end of a capacitor 156 and each collector of NPN transistors 157 and 158. An emitter of the transistor 157 is connected to the electrode K and a collector of an NPN transistor 160, and an emitter of the transistor 158 is connected to the electrode F and a collector of an NPN transistor 159.

On the other hand, the negative end of the battery 151 is grounded and connected to the signal processor 152, an emitter of the transistor 154, the other end of the capacitor 156, and each emitter of the transistors 159 and 160.

The signal processor 152 generates three drive pulses S21, S22, and S23. The drive pulse S21 (signal C1 in FIG. 1) is input to a base of the transistor 154; the drive pulse S22 (signal C2 in FIG. 1) is input to each base of the transistors 157 and 159; and the drive pulse S23 (signal C2 in FIG. 1) is input to each base of the transistors 158 and 160.

Next, the operation of the apparatus shown in FIG. 16 will be described with reference to FIGS. 17a to 17c, which show the signal waveform of each point in the apparatus.

In the illustrated example, boosted pulses generated by the inductive operation of the inductor 153 and the ON and OFF operation of the transistor 154 are accumulated via the diode 155 in the capacitor 156.

When the drive pulse S22 is at a high level and the drive pulse S23 is at a low level, the transistors 157 and 159 are made ON and the transistors 158 and 160 are made OFF. Accordingly, the charges corresponding to the boosted pulses accumulated in the capacitor 156 flow through the transistor 157, electrode K, load or organism RZ, electrode F, and transistor 159, and as a result, the L.F. output pulse $V_{OUT}$ appears across the electrodes K and F in the positive form, as shown in FIG. 17c.

On the other hand, when the drive pulse S22 is at a low level and the drive pulse S23 is at a high level, the transistors 158 and 160 are made ON and the transistors 157 and 159 are made OFF. Accordingly, the charges accumulated in the capacitor 156 flow through the transistor 158, electrode F, load or organism RZ, electrode K, and transistor 160, and as a result, the L.F. output pulse $V_{OUT}$ appears in the negative form, as shown in FIG. 17c.

Therefore, by ensuring that the signal processor 152 can output the drive pulse S22 or S23, the polarity of the L.F. output pulse $V_{OUT}$ can be readily inverted.

Next, a variety of output forms according to the apparatus of the present invention will be explained with reference to FIGS. 18a to 21h. Note, the explanation of the change in the internal operation of the signal processor occurring due to the change in the pulse width or interval of the drive pulses C1 and C2 will be omitted.

FIGS. 18a and 18b show the case in which the drive pulse C2 is intermittently output from the processor. FIG. 18a indicates an output waveform of the drive pulse C2, and FIG. 18b indicates a waveform of the L.F. output pulse.

FIGS. 19a and 19b show the case in which the pulse width of the drive pulse C2 output from the processor is gradually extended or reduced. FIG. 19a indicates an output waveform of the drive pulse C2, and FIG. 19b indicates a waveform of the L.F. output pulse.

Since the width of the L.F. output pulse contributes to the intensity of the acenesthesic stimulation effect, the present example can realize the same touch as that when the skin is massaged.

FIGS. 20a and 20b show the case in which the pulse width of the drive pulse C2 is constant and the pulse interval thereof is changed. FIG. 20a indicates an output waveform of the drive pulse C2, and FIG. 20b indicates a waveform of the L.F. output pulse.

FIGS. 21a to 21e show the case in which the processor changes the output interval of the drive pulse C2, causes the accumulating means to accumulate boosted pulses, and to discharge the accumulated pulses in the course of the rise in voltage, and changes the voltage of the L.F. output pulse. FIG. 21a indicates a waveform of the drive pulse C1; FIG. 21b a waveform of boosted pulse; FIG. 21c a waveform of the terminal voltage of the accumulating means, e.g. capacitor; FIG. 21d a waveform of the drive pulse C2; and FIG. 21e a waveform of the L.F. output pulse.

Also, FIGS. 21f to 21h show the case in which the processor makes the pulse width and interval constant, changes the number of output of the drive pulse C1, changes the voltage of the capacitor for accumulating boosted pulses, and causes an output of the L.F. output pulse. FIG. 21f indicates a waveform of the drive pulse C1; FIG. 21g a waveform of the drive pulse C2; and FIG. 21h a waveform of the L.F. output pulse.

As described above, the present invention is intended to provide an L.F. curing apparatus which can apply a variety of acenesthesic low frequency stimulation effects to an organism over a long period of time, and is constituted by a simple electronic circuit. Also, each constituent element employed in the apparatus can be located on a chip, and furthermore, it is possible to use such a chip to utilize a custom IC and hybrid technique which can be practically adapted for use in various fields.

Thus, the electronic elements employed in the apparatus of the present invention can be mounted on a chip with a high density, and since the techniques such as a gate array, BI-CMOS, HIC and the like can be employed, it is possible to reduce the whole size of the apparatus, i.e. chip, to a maximum size of 20 mm L, 20 mm W, and 5 mm H.

Examples of the overall construction including a low frequency pulse generating apparatus or means will be hereinafter explained with reference to FIGS. 22a, 22b and 23.

Figure 22A:
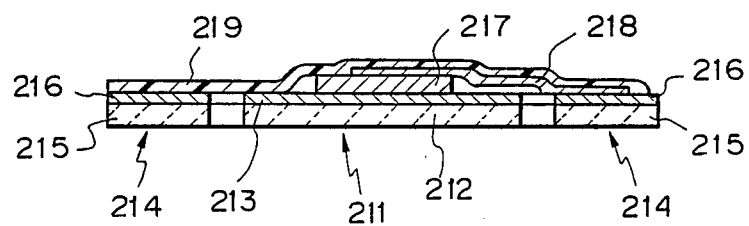
FIGS. 22a and 22b are views showing an example of the overall construction of the apparatus of the present invention.
Figure 22B:
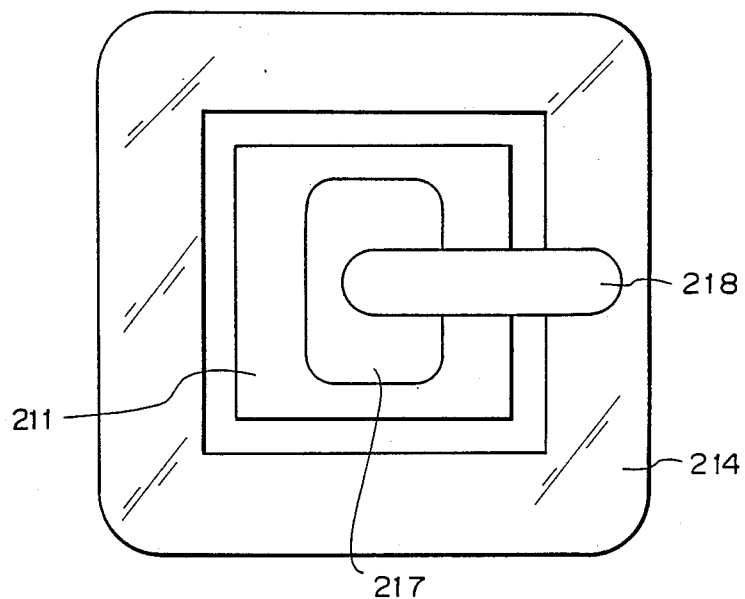

Referring to FIGS. 22a and 22b, which are, respectively, a sectional view and a plan view, reference 211 denotes an electrode participating in the curing which corresponds to the electrode K shown in the drawings, and reference 214 denotes an electrode not participating in curing which corresponding to the electrode F shown in the drawings.

The electrode 211 is integrally formed by laminating a skin-adhesive conductive gel layer 212 formed into a flexible sheet or film and a conductive material layer 213 formed by a metal foil such as an aluminum foil, conductive rubber, resin film, carbon film, conductive paint or the like. Also, the electrode 214 is integrally formed by laminating a skin-adhesive conductive gel layer 215 formed into a flexible sheet or film and a conductive material layer 216 formed by the above aluminium foil or the like. A low frequency pulse generating means 217 is mounted approximately in the center of the upper surface of the electrode 211. This means 217 is provided to include a light weight power source, e.g., a button-type battery, and to place one output terminal thereof, e.g., the minus terminal, in contact with the conductive material layer 213. Also, the plus terminal of this means 217 is connected to the conductive material layer 216 of the electrode 214 through a lead line 218 of, for example, aluminium foil, the lower surface of which is coated with insulating material except in the vicinity f the side ends of the unit. An insulating backing layer 219 consists of, for example, non-conductive synthetic resins formed into a flexible sheet or film. The electrode 211 and the electrode 214 are arranged apart from each other on the insulating backing layer 219 and stuck to the layer.

Namely, the electrodes 211 and 214 and the L.F. pulse generating means 217 are supported and integrally linked by the insulating backing layer 219.

Next, the operation and use of the skin-adhesive type low frequency curing apparatus constructed as described above will be explained. First, the apparatus is applied to the position requiring a cure on the body, so that the electrode 211 is in contact with that position. At this time, the electrode 211 and the electrode 214 constitute a closed circuit, and thus the constitution in which pulses can be oscillated is realized, and as a result, low frequency pulses can be applied via the electrode 211 to the body.

According to the present example, it is possible to obtain a skin-adhesive type low frequency curing apparatus which can be applied directly to the body skin, easily operated, is light-weight, and can provide satisfactory curing effects.

Next, another example of the overall construction will be described with reference to FIG. 23. Note, the explanation of the members indicated by the same references as those employed in FIGS. 22a and 22b will be omitted.

Figure 23:
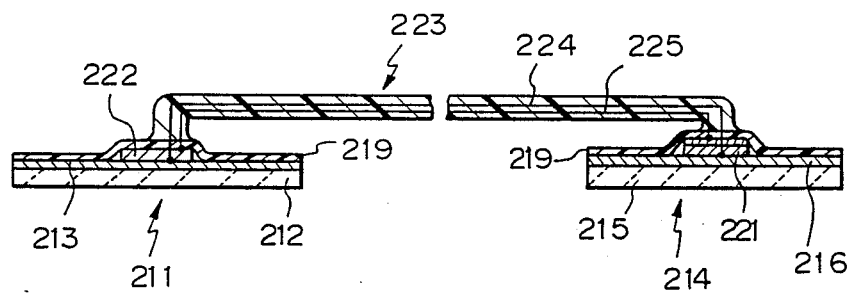
FIG. 23 is a view showing another example of the overall construction of the present invention.

In FIG. 23, reference 221 denotes a button-type battery, and reference 222 denotes an L.F. pulse generating circuit which is located on the conductive material layer 213 of the electrode 211 and connected thereto. On the other hand, the battery 221 is located on the conductive material layer 216 of the electrode 214 and connected thereto. The battery 221 and the L.F. pulse generating circuit 222 are connected through lead lines 224 and 225 within a linking member 223.

According to the present example, since the electrode 211 and the electrode 214 can be applied to the body with a suitably spaced distance within the length of the lead lines 224 and 225, it is possible to use the apparatus even when the region on which it is to be applied is small or has a relatively great curvature. Also, even if the skin sweats greatly during use in hot and humid conditions, the electrodes are not influenced by the current flowing through the epidermis since they are spaced apart, and thus a good skin-adhesive low frequency curing apparatus can be obtained.

Additionally, for the skin-adhesive conductive gel the gel disclosed in, for example, the following publications, is preferably used.

Japanese Unexamined Patent Publication (J.U.P.P.) No. 52-95895, J.U.P.P. No. 54-77489, J.U.P.P. No. 55-52742, J.U.P.P. No. 55-81635, J.U.P.P. No. 55-129035, J.U.P.P. No. 56-15728, J.U.P.P. No. 56-36939, J.U.P.P. No. 56-36940, J.U.P.P. No. 56-60534, J.U.P.P. No. 56-89270, J.U.P.P. No. 57-55132, J.U.P.P. No. 57-131428, J.U.P.P. No. 57-160439, J.U.P.P. No. 57-164064, J.U.P.P. No. 57-166142, J.U.P.P. No. 57-168675, J.U.P.P. No. 57-4569, J.U.P.P. No. 58-10066, Japanese Unexamined Utility Model Publication (J.U.U.M.P.) No. 54-80689, J.U.U.M.P. No. 56-135706, J.U.U.M.P. No. 56-138603, J.U.U.M.P. No. 57-93305, J.U.U.M.P. No. 57-179413, J.U.U.M.P. No. 57-185309.

Although the present invention has been disclosed and described by way of various embodiments, it is apparent to those skilled in the art that other embodiments and modifications of the present invention are possible without departing from the spirit or essential features thereof.

What we claim:

1. A low frequency curing apparatus comprising:
a small-sized power source;
boosted pulse generating means connected to said small-sized power source, for generating a train of boosted pulses having pulse widths and pulse intervals corresponding to first pulse signals;
accumulating means connected to said boosted pulse generating means for accumulating electrical energy to at least a predetermined amount for electrically stimulating an object;
low frequency pulse outputting means connected to said accumulating means, for outputting low frequency pulses having pulse widths and pulse intervals corresponding to second pulse signals, the low frequency pulses having an amplitude corresponding to the electrical energy accumulated in said accumulating means;
a pair of electrode members having planar portions for transmitting the low frequency pulses from said low frequency pulse outputting means to said object; and
signal processing means connected to said small-sized power source and including a predetermined algorithm for outputting the first pulse signals and the second pulse signals, wherein at least one of the first and second pulse signals have at least one of a changeable pulse width and pulse interval in accordance with the predetermined algorithm, whereby a variety of low frequency stimulation effects are applied to said object to be stimulated.

2. An apparatus as set forth in claim 1, wherein said small-sized power source, boosted pulse generating means, accumulating means, low frequency pulse outputting means and signal processing means constitute a low frequency pulse generating apparatus, and at least one of said pair of electrode members if formed integral with said low frequency pulse generating apparatus.

3. An apparatus as set forth in claim 2, further comprising de-polarization means for discharging polarization charges remaining within said object after said low frequency pulses are applied to said object.

4. An apparatus as set forth in claim 3, wherein said signal processing means generates control signals based on the generation of said second pulse signals, and said de-polarization means includes a means for short-circuiting said pair of electrode members in response to said control signal.

5. An apparatus as set forth in claim 4, wherein said signal processing means includes an inverter for generating said control signal from said second pulse signal, said low frequency pulse outputting means includes a transistor responding to said second pulse signal and transmitting energy accumulated in said accumulating means to said pair of electrode members, and said de-polarization means includes a transistor responding to said control signal.

6. An apparatus as set forth in claim 2, wherein said low frequency pulse outputting means includes a switching means operated in response to said second pulse signal, and said accumulating means includes a plurality of capacitors, said plurality of capacitors being connected in series via said switching means when said second pulse signal is at a predetermined logic level, whereby electrical energy accumulated in said accumulating means in series connection is conducted as low frequency pulses.

7. An apparatus as set forth in claim 2, wherein the generated second pulse signals of said signal processing means includes either a first drive signal or a second drive signal, and said low frequency pulse outputting means includes a switching means responsive to said first and second drive signals for switching the transmission of energy accumulated in said accumulating means to a respective one and the other of said pair of electrode members.

8. An apparatus as set forth in claim 1, further comprising starting means including a plurality of switches for selecting an operation mode and applying input information to said signal processing means corresponding to the selected operation mode.

9. An apparatus as set forth in claim 8, wherein said signal processing means comprises, a microcomputer responsive to the input information, in the form of a chip, including a first memory means for storing a program defining the predetermined algorithm and for executing the operation of the predetermined algorithm and a second memory means for storing a plurality of variable parameters, said microcomputer operating in response to said input information for changing the at least one pulse width and pulse interval of said at least one first and second pulse signals in accordance with the variation of said parameters stored in said second memory means.

10. An apparatus as set forth in claim 8, wherein said signal processing means includes control means for starting and stopping the operation of said apparatus in response to a first portion of said input information, an oscillator governed by said control means for generating a chain of clock pulses, means for generating a plurality of false signals, each having a frequency lower than said clock pulses and having a frequency different form one another, and a selection means responsive to a second portion of said input information for selecting a predetermined number of pulse signals among said plurality of pulse signals and outputting said first and second pulse signals based on said selected pulse signals.

11. An apparatus as set forth in claim 10, wherein the pulse width of said first and second pulse signals is defined by said second portion of said input information, and the pulse intervals of the first and second pulse signals is defined by said means for generating a plurality of pulse signals.

12. An apparatus as set forth in claim 10, wherein said second portion of said input information includes voltage information from said small-sized power source, and wherein said selection means increases the pulse width of said first pulse signal at times when said voltage information indicates a drop in voltage of said power source.

13. An apparatus as set forth in claim 10, wherein said selection means comprises a capacitor and a resistance circuit having a time constant that varies in response to part of said second portion of said input information, and said second pulse signals have a pulse width corresponding to the tie constant.

14. An apparatus as set forth in claim 10, further comprising a detecting means for detecting electrical energy accumulated in said accumulating means and outputting a detection signal at times when said accumulated energy reaches a predetermined amount, and said signal processing means includes means changing the form of the generation of said first pulse signals in response to said detection signals.

15. An apparatus as set forth in claim 14, wherein the second portion of said input information includes the detection signal, and said selection means selects pulse signals for the generation of said first pulse signals in response to said detection signals.

* * * * *